United States Patent [19]

Coe

[11] Patent Number: 4,883,972
[45] Date of Patent: Nov. 28, 1989

[54] MONITORING EQUIPMENT FOR DETECTION OF EMISSION

[75] Inventor: Charles D. Coe, Chesterfield, England

[73] Assignee: Combustion Developments Limited, Derbyshire, England

[21] Appl. No.: 190,757

[22] Filed: May 6, 1988

[30] Foreign Application Priority Data

May 13, 1987 [GB] United Kingdom ............... 8711309

[51] Int. Cl.$^4$ ..................... G01N 21/00; G01N 21/49
[52] U.S. Cl. .................................... 250/575; 356/343
[58] Field of Search ............... 250/574, 575; 356/337, 356/338, 339, 340, 341, 342, 343; 340/630

[56] References Cited

U.S. PATENT DOCUMENTS 3,535,533 10/1970 Guidi .................................. 250/575
4,647,785 3/1987 Morita ................................ 250/574

Primary Examiner—David C. Nelms
Assistant Examiner—William L. Oen
Attorney, Agent, or Firm—R. A. Giangiorgi

[57] ABSTRACT

The invention relates to monitoring equipment for smoke and/or fine particle emissions from fossil fuel systems, of the type where a beam of visible light is passed across a flue from a light source to a detector, a difference in the light intensity received by the detector from the known intensity of the source indicating absorption of light by smoke and/or fine particles in the flue, and the degree of difference indicating the level of smoke and/or fine particles. The objective of the invention is to provide monitoring equipment of the above type, of simpler, lower cost, more robust nature than has hitherto been provided. The objective is met by a construction comprising two units (1, 2) for location of opposite sides of a flue or chimney each unit comprising a light source, ($L_1$, $L_2$) a lens (4) and a light detector ($D_1$, $D_2$), the light from the light source of each said unit being directed by its lens across the flue or chimney in a divergence path, to be gathered by the lens of the opposite unit and directed to the detector in the opposite unit, the outputs from the detectors of each unit being combined to provide a reading of the degree of smoke and/or fine particulate material existing in the flue or chimney.

11 Claims, 2 Drawing Sheets

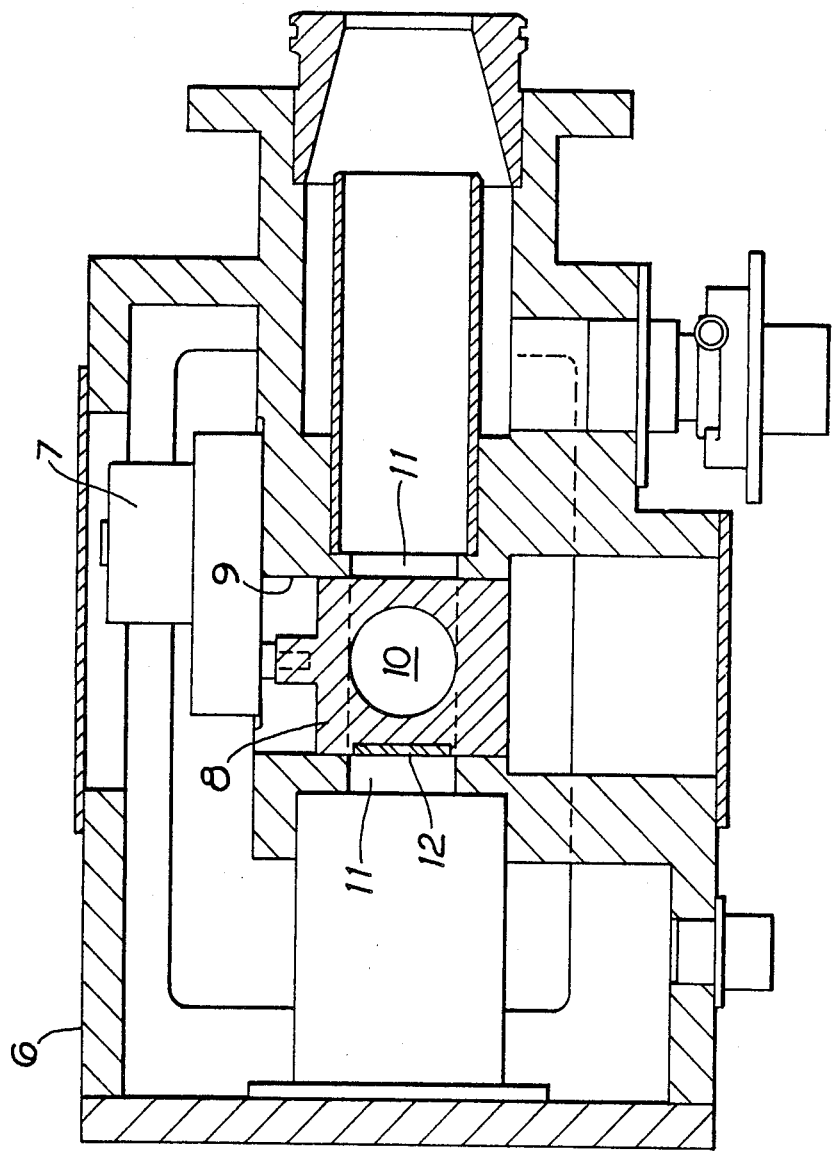

MONITORING EQUIPMENT FOR DETECTION OF EMISSION

This invention relates to monitoring equipment and is particularly although not necessarily exclusively concerned with the monitoring of smoke and fine particulate material (dust) emissions from fossil fuel combustion systems.

It has long been recognised that there is a need to control smoke and dust emissions to the atmosphere, and as a means of achieving this it has already been proposed to monitor smoke and dust passing through a flue or a chimney extending from the combustion system and to use the readings from such monitors as a means of checking the emission levels and combustion efficiency of the fuel combustion systems.

Thus, it is already known to provide on a flue or a chimney a means of projecting a beam of visible light across the flue or chimney from a light source to one side to a detector at the other, or to provide a light source and a detector to the same side of a flue or chimney and a reflecting mirror at the other, such systems operating on the principle that light is absorbed by any smoke or dust existing in the flue or chimney it being the difference between the known intensity of the light source and the lower intensity of light measured by the detector that is used to calculate the degree of smoke of dust existing in the flue or chimney.

Such systems that are primarily intended for the detection of smoke need not be particularly accurate and can be of relatively simple construction and of relatively low cost. However, such systems that are to provide effective monitoring of dust existing in a flue or chimney need to be of much greater accuracy and tend to be complex structures of relatively high cost. Thus, in certain circumstances it is necessary for there to be a degree of accuracy of alignment as between the light source and detector or the light source, the reflecting mirror and the detector that is within 0.5 degrees and circumstances where even closer control is needed and where that degree of accuracy must be within 0.1 degrees. This of itself constitutes a major problem in the construction of such equipment and in its installation and operation on a flue or chimney.

It is also the case that with such systems it is necessary for there to be periodic calibration, and here it is known to introduce a reflecting mirror that can be introduced between the light source and the flue or chimney to reflect light onto the detector and hence eliminate the flue or chimney from the sight path. Here the difficulty is that if the calibrating mirror becomes contaminated with dirt inaccurate calibration takes place. It is equally the case that the insertion of a calibrating mirror provides no means of checking the alignment between the light source and its detector, nor does it check for the effects of contamination of the reflector on the opposite side of the flue or chimney.

One object of the invention is to provide monitoring equipment of a relatively simple and relatively low cost character and where considerably greater tolerance of alignment is provided as between a light source and a detector. Another object of the invention is to provide a means of ensuring the absence of contamination of a calibrating mirror. Other objectives of the invention will become apparent on reading the following text.

According to a first aspect of the present invention monitoring equipment for smoke and/or fine particulate material emissions comprises two units for location to opposite sides of a flue or chimney each unit comprising a light source, a lens and a light detector, the light from the light source of each said unit being directed by its lens across the flue or chimney in a divergence path, to be gathered by the lens of the opposite unit and directed to the detector in the opposite unit, the outputs from the detectors of each unit being combined to provide a reading of the degree of smoke and/or fine particulate material existing in the flue or chimney.

To provide a means of calibrating each unit, a reflecting mirror can be introduced between each unit and the flue or chimney. In a relatively low cost unit, particularly for the monitoring of smoke, the reflecting mirror can be manually applied and removed, giving the opportunity of cleaning the mirror before calibration takes place. However, when monitoring dust is required, it is frequently so that automatic calibration must be provided for. Thus, in accordance with a second aspect of the invention a means of preventing the contamination of a calibrating mirror comprises locating a calibrating mirror on a plug member rotatable within a housing, said plug member having a through hole with an axis parallel to the plane of the mirror the plug member being rotatable from a first position where the through hole provides a sight path between a light source and a directing lens and when the mirror lies within the housing, to a second position where the mirror is located in the sight path to reflect light from the light source to a strategically located detector. Rotation of the plug and its mirror can be effected by any suitable means, such as by a solenoid or by a stepping motor.

Preferably, the light source in each said unit is a high intensity light emitting diode (LED) and which has the threefold advantage of a long working life, only requiring low power for effective operation, and can be modulated electronically to provide pulsed light at an effective wavelength for the light, and which is further preferably between 500 and 700 nanometers in the visible spectrum. The ability to provide required pulsed frequencies has the advantage that the light source in each unit can be pulsed at two different frequencies, and the detector signals can be separated into the components of those frequencies, to enable the precise identification of the light from each source and additionally allow the elimination of the effects of any stray light source that is received by either detector.

Alternatively, the two light sources can be modulated by signals produced by combining the two different frequencies in such a way that the light source of one unit is modulated by the AND function of the two frequencies whilst the light source of the other unit is modulated by the AND function of one frequency and the inverse of the other frequency. In this way, only one light source is illuminated at any one time, thereby simplifying the means of identifying the light from each source.

The invention avoids the need to reflect light back across the flue or chimney and hence avoids potential problems by contamination present on a main reflecting mirror and which would have an inevitable effect on the readings provided by the system. By directing light across the flue or chimney in a diverging manner the degree of alignment as between the units to each side of the flue or chimney is considerably less critical than in any system known hitherto. Dependent upon the particular lens and the angle of divergence of the light beam, misalignment as high as 30 can be tolerated without affecting the accuracy of the readings from the system. It is equally so that in addition to being able to tolerate a degree of misalignment, the system also allows for the automatic checking that misalignment is not at an unacceptably high level as will be discussed below.

By providing light sources and detectors to each side of the flue or chimney and directing light beams in opposite directions across the flue or chimney, an by combining the outputs from the detectors of each unit, there is the automatic self-compensation for any detector drift. In addition to this, by employing LED's as the light sources, there is a considerable simplification in effecting periodic span checks as are required to check the response of the detectors to any change in the intensity emitted by the light sources. Thus, instead of, as has hitherto been necessary, the need to insert neutral density filters into the sight path between a light source and its detector, the ease of electronic modulation of the LED's allows light intensity to be varied as a means of checking the detectors reaction to such variation. In addition to the above, at the calibration stage, the introduction of a calibrating mirror between each unit and the flue or chimney allows the checking for any contamination present on any of the optical surfaces of the system.

One embodiment of invention will now be described briefly and further explained by way of example only, with reference to the accompanying drawings, in which:

FIG. 2 is a sectional side elevation of one embodiment of calibrating lens mounting means.

Figure 1:
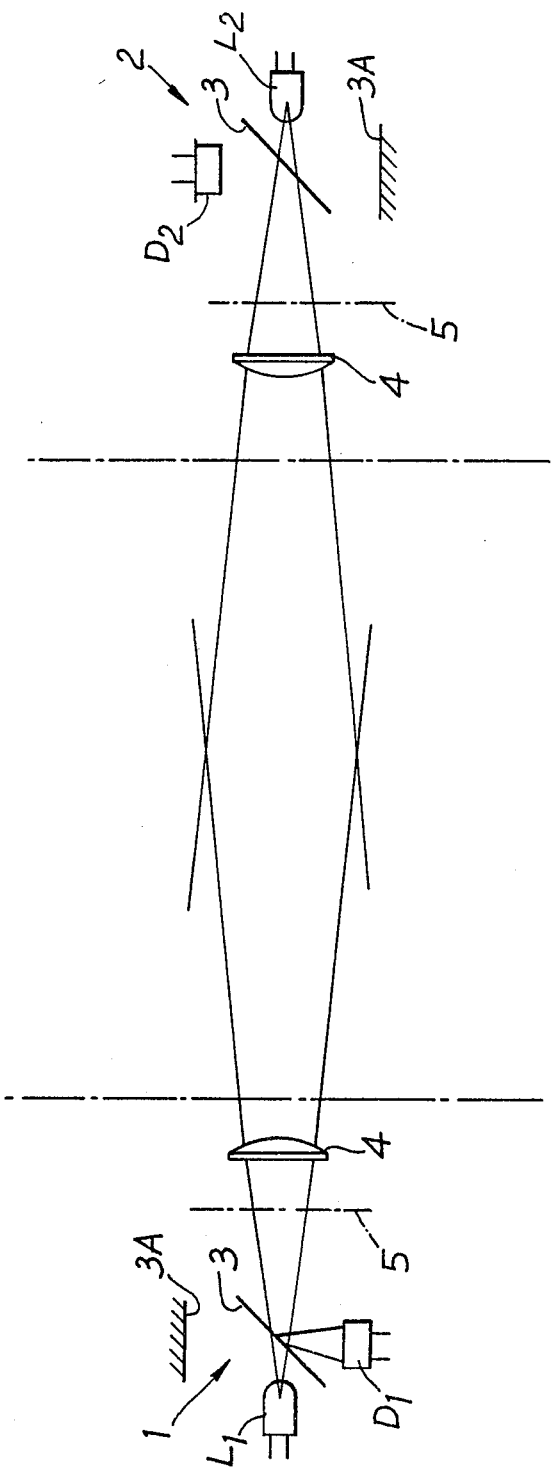
FIG. 1 is a schematic view of the invention located on a flue or chimney.

In FIG. 1 there is the schematic representation of the monitoring system of the invention. Thus, to each side of a flue or chimney units 1 and 2 are provided, the unit 1 having a light source $L_1$ and a light detector $D_1$, and the unit 2 having a light source $L_2$ and a light detector $D_2$. In each unit a beam splitter 3 is provided to allow a light beam to be transmitted across the flue or chimney, and to direct incoming light on to detector $D_1$ or $D_2$. Each unit 1 and 2 has a lens 4, to direct a light beam across the flue or chimney in a divergent path, and to gather incoming radiation for direction at the beam splitter 3. It will therefore be immediately apparent that considerable latitude is permitted in the alignment of the two units because of divergent light beams passing across the flue or chimney. The beam splitters 3 additionally direct light from the light sources $L_1$ and $L_2$ to mirrors 3A for reflection back to the respective detectors $D_1$ and $D_2$ of the units each detector being such as to be capable of receiving and distinguishing between the radiation from both light sources, and when calibration of the system is required, a mirror 5 can be introduced manually or automatically between the lens and the flue or chimney and when light from each light source $L_1$ and $L_2$ is reflected back to the detector $D_1$ and $D_2$ respectively. The two transmitter/receiver units 1 and 2 have identical optical configurations. Each consists of an LED and a silicon detector arranged as shown in FIG. 1. Each detector can monitor light received from both its own neighbouring LED and that transmitted from the opposite unit. By modulating the two LEDs at different frequencies the two light levels can be resolved by phase sensitive detection techniques.

In a first operating mode and during normal operation to monitor the amount of smoke and/or dust present in the flue or chimney, the transmissivity of light from Unit 1 to Unit 2 is obtained from the relation $$T_{1,2} = G_1 \cdot (D_2/D_1) f_1$$

where $G_1$ is a gain constant to produce $T=1$ for a clean stack condition and $D_2$ is the signal provided by detector $D_2$ from light transmitted from LED 1 at frequency $f_1$, while $D_1$ is the signal provided by detector $D_1$ from LED 1 at frequency $f_1$.

The transmissivity of light from Unit 2 to Unit 1 is $$T_{2,1} = G_2 \cdot (D_1/D_2) f_2$$

$G_2$ is a gain constant and $D_1$ is the signal provided by detector $D_1$ from light received from LED 2 at frequency $f_2$; $D_2$ is the signal provided by detector $D_2$ from LED 2 at frequency $f_2$.

The resultant transmissivity of the light over the two passes is obtained from the expression $$T = T_{1,2} \times T_{2,1}$$

$$T = G_1 G_2 (D_2/D_1) f_1 \cdot (D_1/D_2) f_2$$

and Opacity $= 100 \ [1 - G_1 G_2 (D_2/D_1) f_1 \cdot (D_1/D_2) f_2 \ ]\%$

The measurement can thus be made independant of any drift of either detector 1 or detector 2.

The required calibration check can be made at each unit by placing a mirror in front of each lens. Consider first Unit 1. The detector output when the calibration mirror is in place is $$D_{1cal} = D_1 + K \cdot D_1 \cdot T_1^2$$

where $T_1$ is the transmissivity of the lens surface (Note the double pass requires $T_1^2$) and K is a constant depending upon the reflectivities of the internal optical system. $D_1$ is the detector output from light from LED 1 at frequency $f_1$ immediately prior to the calibration mirror being inserted.

Thus $T_1^2 = (D_{1cal} - D_1)/K \cdot D_1$ from which function the effective lens contamination can be calculated. The constant K is set to produce $T_1 = 1$ for a clean lens condition.

Lens contamination $= 100[1 - T_1^2]\%$

This calibration procedure can also be made for Unit 2 enabling the contamination of each lens to be monitored and if necessary compensated for.

Note that the double pass applies both for the calibration procedure and for the normal measurement mode which is also effectively a double pass system since the transmissivity of light from Unit 1 to 2 taking into account the transmissivity of the lens is $$T'_{12} = T_{12} \cdot T_1 \cdot T_2$$

and from Unit 2 to 1 is $$T'_{21} = T_{21} \cdot T_2 \cdot T_1$$

Thus the combined double pass transmissivity is $$T' = T_{12} \cdot T_{21} \cdot T_1^2 \cdot T_2^2$$

$$T' = T^2 \cdot T_1^2 \cdot T_2^2$$

The zero check output for the system may be displayed as $$zero = 100(1 - T_1^2 \cdot T_2^2)\%$$

since at zero opacity the transmissivity T=1.

In a second operating mode the two LEDs are modulated by signals produced by combining the two different frequencies $f_1$ and $f_2$ in such a way that LED 1 is modulated by the AND function of $f_1$ and $f_2$ while LED 2 is modulated by the AND function of $f_1$ and the inverse of $f_2$ ($\bar{f_2}$). In this way only one LED is illuminated at any one time thus enabling the signals from each detector to be resolved into the components received from LED 1 and LED 2. In this case the following applies. During normal operation to monitor the amount of smoke and/or dust present in the flue or chimney, the transmissivity of light from Unit 1 to Unit 2 is obtained from the relation $$T_{1,2} = G_1 \cdot D_{21}/D_{11}$$

where $G_1$ is a gain constant to produce T=1 for a clean stack condition and $D_{21}$ is the signal provided by detector $D_2$ from light transmitted from LED 1, while $D_{11}$ is the signal provided by detector $D_1$ from LED 1.

The transmissivity of light from Unit 2 to Unit 1 is $$T_{2,1} = G_2 \cdot D_{12}/D_{22}$$

$G_2$ is a gain constant and $D_{12}$ is the signal provided by detector $D_1$ from light received from LED 2; $D_{22}$ is the signal provided by detector $D_2$ from LED 2. The resultant transmissivity of the light over the two passes is obtained from the expression $$T = T_{1,2} \times T_{2,1}$$

$$T = G_1 G_2 (D_{21}/D_{11}) \cdot (D_{12}/D_{22})$$

and Opacity = $100[1 - G_1 G_2 (D_{21}/D_{11}) \cdot (D_{12}/D_{22})]\%$

The measurement can thus be made independent of any drift of either detector 1 or Detector 2.

The required calibration check can be made at each unit by placing a mirror in front of each lens. Consider first Unit 1.

The detector output when the calibration mirror is in place is $$D_{11cal} = D_{11} + K \cdot D_{11} \cdot T_1^2$$

where $T_1$ is the transmissivity of the lens surface (Note double pass requires $T_1^2$) and K is a constant depending upon the reflectivities of the internal optical system. $D_{11}$ is the detector output from the light from LED 1 immediately prior to the calibration mirror being inserted.

Thus $T_1^2 = (D_{11cal} - D_{11})/K \cdot D_{11}$ from which function the effective lens contamination can be calculated. The constant K is set to produce $T_1 = 1$ for a clean lens condition.

Lens contamination = $100[1 - T_1^2]\%$

This calibration procedure can also be made for Unit 2 enabling the contamination of each lens to be monitored and if necessary compensated for.

Note that the double pass applies both for the calibration procedure and for the normal measurement mode which is also effectively a double pass system since the transmissivity of light from Unit 1 to 2 taking into account the transmissivity of the lens is $$T'_{12} = T_{12} \cdot T_1 \cdot T_2$$

and from Unit 2 to 1 is $$T'_{21} = T_{21} \cdot T_2 \cdot T_1$$

Thus the combined double pass transmissivity is
$$T' = T_{12} \cdot T_{21} \cdot T_1^2 \cdot T_2^2$$

$$T' = T^2 \cdot T_1^2 \cdot T_2^2$$

The zero check output for the system may be displayed as $$\text{zero} = 100 \ (1 - T_1^2 \cdot T_2^2)\%$$

since at zero opacity the transmissivity T=1.

In addition to periodic calibration checks, periodic span checks are required to test the reaction of the detection system to a change in transmitted light intensity. The result of such a check is to provide a test of the reproducibility of the detector response to such a change. Hitherto, neutral density filters have needed to be introduced in the sight path from a light source to its detector, but this introduces additional moving components, and the span check point can be adjusted only by changing the filter characteristic. By providing LED's the light output of which can be changed with relative ease e.g., by reducing the current to the LED's enables the calibration point to be easily selectable. In this situation if "m" is the reduction ratio of the LED current the detector output during the span check point of the cycle becomes $$D_1 \text{span} = m \cdot D_{1cal}$$

where $D_{1cal}$ is the zero check detector level found during the zero check cycle immediately preceding.

The span check output of the system can be shown as $$\begin{aligned} T\text{span} &= 100(1 - m_1 \cdot m_2) \\ &= 100(1 - D_1\text{span}/D_1\text{cal} \times D_2\text{span}/D_2\text{cal}) \end{aligned}$$

$m_1$ and $m_2$, the reduction ratios of the span check LED currents, can be selected to provide a span check at any point on the instrument scale, for any range of output, without the need to select and change optical filters as with existing equipment. Additionally since $m_1$ and $m_2$ are both checked independently any error can be immediately traced to one of the two units.

As has been mentioned previously the output of the instrument is independent of drift of either detector D1 or D2. However the characteristics of silicon cell detectors used in this system are such that drift with temperature is virtually eliminated by the use of a specific wavelength of light remote from the silicon cell long wavelength cut off point at approximately 1100 nanometers which is the temperature sensitive part of the cell characteristic. This means that while the instrument is still independent of detector drift it is still possible to keep such drift down to a minimum. This enables transmissivity measurements to be assessed for each direction of transmission creating the possibility of detecting changes in optical alignment.

The two measurements of transmissivity (one in each direction) are made simultaneously over the same path and should consequently give the same value. Note that any contamination of either of the optical surfaces will affect each transmissivity measurement identically.

If a condition arises where an angular deflection is applied to one of the transmitter/receiver units, due to movement of the boiler duct for example, the illuminated field of that transmitter will eventually begin to miss its target, the lens of the opposite unit. The detector of the opposite unit will consequently monitor a lower signal which will be interpreted as a lower transmissivity. The transmissivity measurement in the opposite direction however is unaffected by that angular deflection. Thus a disparity will occur between the two transmissivity values. Since such errors when they do occur are likely to be substantially larger than the minimal errors due to detector drift, they can be immediately identified.

Should both transmitter/receiver units be misaligned, the principle still applies since it is extremely unlikely that both units would experience the same degree of error; a difference would still identify the condition.

In circumstances where automatic calibration is required, e.g., in the monitoring of dust, the permanent location of a calibrating mirror in the vicinity of the flue or chimney can have the effect of the calibrating mirror being contaminated with an inevitable effect on the zero calibration check. Thus, of independent significance, is the construction exemplified in FIG. 2 and which shows a means of keeping a reflecting mirror free from contamination. Thus, in FIG. 2 is shown a housing 6 within which is a stepping motor 7 secured to and able to rotate when required, a cylidrical plug member 8 located in a cylindrical bore 9. The plug member 8 has a through bore 10 to align with ports 11 in the walls of the bore and a reflecting mirror 12 set within a recess in the wall of the plug, with the plane of the mirror parallel to longitudinal axis of the through bore 10. Thus, when used in the monitoring system of the invention, the plug can be set in a position such that the through bore 10 is aligned with the ports 11, to provide a continuous sight path from a light source to a detector located within the housing. In this position, the mirror lies wholly within the cylindrical bore 9 and is thus shielded and substantially prevented from being contaminated. When a calibration check is required, the stepping motor is activated to rotate the plug member 8 to bring the clean reflecting mirror into position, the through bore 10 now being closed by the cylindrical bore 9 again to prevent any contaminants from reaching the mirror 12.

I claim:

1. Monitoring equipment for smoke and/or fine particulate emissions in which light from a light source is transmitted across a flue to a detector, comprising two units for location to opposite sides of a flue or chimney, each unit comprising a light source, a lens and a light detector, the light from the light source of each said unit being directed by its lens across the flue or chimney in a divergence path, to be gathered by the lens of the opposite unit and directed to the detector in the opposite unit, and there being means in each unit to direct light from said light source to said respective detector, and means for combining the outputs from the detectors of each unit to provide a resulting composite reading of the degree of smoke and/or fine particulate material existing in the flue or chimney.

2. Monitoring equipment as in claim 1, wherein a reflecting mirror is introduced periodically into the light path of each unit to reflect light from each light source back to its respective detector, to direct the total output from said light source to said respective detector for the purpose of calibrating each unit.

3. Monitoring equipment as in claim 2, wherein to prevent contamination of the reflecting mirror, the mirror is located on a plug member rotatable within a housing, said plug member having a through hole with an axis parallel to the plane of the mirror, the plug member being rotatable from a first position where the through hole is aligned with the path between one said light source and respective directing lens to a second position where the mirror is located in the said path to reflect light from said light source to said respective detector.

4. Monitoring equipment as in claim 3, wherein the said plug member is positively driven between its first and second positions.

5. Monitoring equipment as in claim 1, wherein the light source of each unit is a light emitting diode.

6. Monitoring equipment as in claim 1, wherein each said light source is modulated to provide pulsed light at a required frequency.

7. Monitoring equipment as in claim 6, wherein the light sources of the units are pulsed are different frequencies.

8. Monitoring equipment as in claim 7, wherein the light source of each unit is modulated by signals produced by combining the different pulsed frequencies in such a way that the light source of one unit is modulated by means for generating an AND function of the two frequencies, and the light source of the other unit is modulated by means for generating an AND function of one frequency and the inverse of the other frequency.

9. Monitoring equipment as in claim 1, wherein to provide a span check, at least one said light source is selected of a type that can vary its output by varying electrical current supplied to it.

10. Monitoring equipment as in claim 1, wherein the detectors of each unit are silicon cell detectors.

11. Monitoring equipment as in claim 1 wherein said means in each unit to direct light from said light source to said detector comprising a beam splitter and an associated mirror.

* * * * *